United States Patent

Böttcher et al.

[11] Patent Number: 6,121,464
[45] Date of Patent: Sep. 19, 2000

[54] PREPARATION OF SALTS OF ASCORBYL 2-PHOSPHORIC ESTERS

[76] Inventors: Andreas Böttcher, Konrad-Adenauer-Ring 38, 69226 Nussloch; Hans Gurski, Im Steigert 3, 67459 Böhl-Iggelheim, both of Germany

[21] Appl. No.: 09/352,139

[22] Filed: Jul. 13, 1999

[30] Foreign Application Priority Data

Jul. 13, 1998 [DE] Germany .................. 198 31 056

[51] Int. Cl.$^7$ ..................................... C07F 9/06
[52] U.S. Cl. ........................................... 549/222
[58] Field of Search ................................ 549/222

[56] References Cited

U.S. PATENT DOCUMENTS

| | | | |
|---|---|---|---|
| 5,110,951 | 5/1992 | Ishimura et al. | 549/222 |
| 5,118,817 | 6/1992 | Yoshida et al. | 549/222 |
| 5,149,829 | 9/1992 | Seib et al. | 549/222 |
| 5,202,445 | 4/1993 | Dobler et al. | 549/315 |
| 5,210,220 | 5/1993 | Pauling et al. | 549/222 |
| 5,212,079 | 5/1993 | Fujio et al. | 435/131 |
| 5,420,302 | 5/1995 | Kaiser et al. | 549/222 |
| 5,516,919 | 5/1996 | Samo et al. | 549/222 |
| 5,578,471 | 11/1996 | Fujio et al. | 435/131 |
| 5,582,739 | 12/1996 | Kaiser et al. | 210/721 |
| 5,849,933 | 12/1998 | Leuenberger | 549/222 |
| 5,916,915 | 6/1999 | Hong et al. | 514/474 |

FOREIGN PATENT DOCUMENTS

| | | |
|---|---|---|
| 229154 | 12/1990 | European Pat. Off. . |
| 582924 | 2/1994 | European Pat. Off. . |
| 2-131494 | 5/1990 | Japan . |
| 9-77784 | 3/1997 | Japan . |
| 8700172 | 1/1987 | WIPO . |
| 9113895 | 9/1991 | WIPO . |

Primary Examiner—Deborah C. Lambkin

[57] ABSTRACT

A process for preparing salts of ascorbyl 2-phosphoric esters of the formula I,

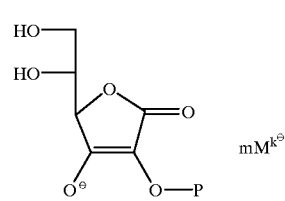

where the variables have the following meanings:

M is sodium, potassium, magnesium, aluminum;

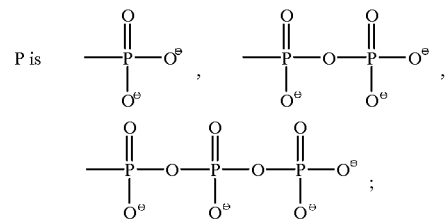

k⊕ is the valence and m=equivalents, where the product of k·m can be from 3 to 5, comprises a) dissolving calcium L-ascorbate-2-phosphate in an aqueous solution of ascorbyl 2-phosphoric esters at a pH of from 0.5 to 4, b) removing the calcium ions from the resulting solution, c) adjusting the pH of the solution which remains to from 7 to 11 by means of sodium, potassium, magnesium or aluminum salts and d) isolating the salts of the ascorbyl 2-phosphoric ester of the formula I.

11 Claims, No Drawings

PREPARATION OF SALTS OF ASCORBYL 2-PHOSPHORIC ESTERS

The present invention relates to a process for preparing salts of ascorbyl 2-phosphoric esters, in particular salts of ascorbyl 2-monophosphoric esters.

L-Ascorbic acid (vitamin C) is among the least stable vitamins both in foods and, for example, cosmetic and pharmaceutical preparations.

In contrast, L-ascorbyl 2-phosphoric esters are an oxidation-stable and bioavailable form of vitamin C. Particularly calcium L-ascorbate-2-monophosphate and calcium L-ascorbate-2-triphosphate are used as stable vitamin C derivatives in animal feed, especially in the feed of aquaculture.

In cosmetics, vitamin C phosphate is used as an antioxidant to protect the skin against free radicals, as a bleaching agent and also as an active compound for improving the elasticity of the skin.

While the sparingly soluble calcium salt is preferred in aquaculture, preference is given to water-soluble salts of ascorbyl 2-phosphoric esters in cosmetic formulations because of the requirement profile. Such water-soluble salts include, inter alia, sodium or magnesium L-ascorbate-2-monophosphate.

The industrial synthesis of calcium L-ascorbate-2-monophosphate or calcium L-ascorbate-2-triphosphate is described, for example, in EP-A-0 229 154, U.S. Pat. No. 5,149,829, EP-A-0 471 805 and EP-A-0 582 924. The process described in EP-A-0 582 924 in particular represents an industrially simple route to calcium L-ascorbate-2-monophosphate of high purity.

In contrast, the synthesis of the water-soluble sodium or magnesium salts of ascorbyl 2-phosphoric ester is significantly more complicated. At present, no processes which can readily be carried out in industry are known for, in particular, such products which have to meet the high purity requirements for use in cosmetic or pharmaceutical preparations.

JP-A-09-077784 and JP-A-02-131494 describe processes for preparing amorphous or crystalline sodium L-ascorbate-2-monophosphate by neutralizing an aqueous solution of ascorbyl 2-monophosphoric esters with aqueous sodium hydroxide solution to a pH of from 7 to 11 or from 8 to 10 and precipitating the sodium L-ascorbate-2-monophosphate formed by adding low molecular weight alcohols or ketones having a carbon chain of $C_1$ to $C_5$ at elevated temperatures.

A problem associated with these processes is the provision of an appropriately pure and industrially readily accessible ascorbyl 2-monophosphoric ester in the protonated form as starting material for the abovementioned conversion into the sodium or magnesium salt. The fractional ion exchange chromatography on a weak base ion exchanger described for this purpose in the two Japanese documents is too complicated for industrial use.

It is an object of the present invention to provide a process for preparing salts of ascorbyl 2-phosphoric esters selected from the group consisting of sodium, potassium, magnesium and aluminum salts, which process can be carried out advantageously on an industrial scale and gives a product quality which meets, inter alia, the strict purity requirements for active compounds in, for example, cosmetics.

We have found that this object is achieved by a process for preparing salts of ascorbyl 2-phosphoric esters of the formula I,

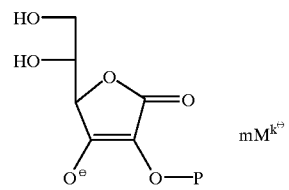

where the variables have the following meanings:
  M is sodium, potassium, magnesium, aluminum;

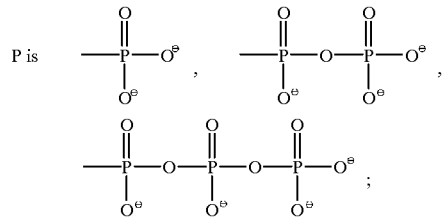

$k\oplus$ is the valence and
  m are equivalents, where the product of k·m can be from 3 to 5,
which comprises
  a) dissolving calcium L-ascorbate-2-phosphate of the formula Ia, where P is as defined above, in an aqueous solution of ascorbyl 2-phosphoric esters of the formula II, where $p^1$ is $H_2PO_3$, $H_3P_2O_6$ or $H_4P_3O_9$, at a pH of from 0.5 to 4,

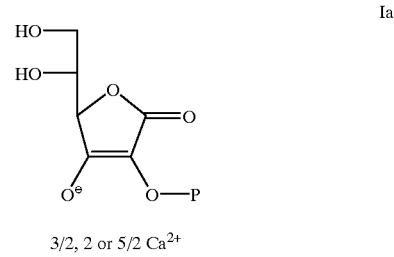

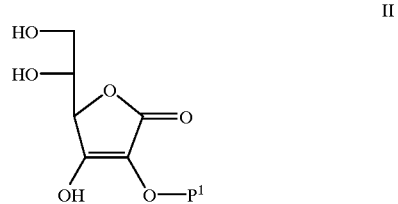

b) removing the calcium ions from the resulting solution,
  c) adjusting the solution which remains to a pH of from 7 to 11 by means of sodium, potassium, magnesium or aluminum salts and
  d) isolating the resulting salts of the ascorbyl 2-phosphoric ester of the formula I.

For the purposes of the present invention, ascorbate-2-phosphate and ascorbyl 2-phosphoric esters are phosphoric esters in general of ascorbic acid in which the hydroxyl group on the $C_2$ carbon of the five-membered ring is esterified by monophosphoric, diphosphoric or triphosphoric acid groups.

The process of the present invention is preferably used for preparing the abovementioned salts of L-ascorbate-2- monophosphate or L-ascorbate-2-triphosphate, particularly preferably for preparing sodium, potassium, magnesium or aluminum L-ascorbate-2-monophosphate.

Starting materials for preparing the abovementioned salts of ascorbyl-2-phosphate by the process of the present invention are calcium L-ascorbate-2-phosphates, preferably the sparingly water-soluble calcium L-ascorbate-2-monophosphate and the corresponding calcium L-ascorbate-2-triphosphate, whose preparation is described, for example, in EP-A-0 229 154, EP-A-0 471 805 and EP-A-0 582 924.

The preparation of the particularly preferred starting material calcium L-ascorbate-2-monophosphate is advantageously carried out as described in EP-A-0 582 924 by $a_1$) reacting ascorbic acid with phosphorus oxychloride in the presence of pyridine while maintaining a pH of from 12 to 13 by means of an aqueous potassium hydroxide solution, $b_1$) precipitating the phosphate ions formed in this reaction as potassium magnesium phosphate by means of magnesium chloride in amounts of from about 0.9 to 1.1 mol per mol of phosphate ions, $c_1$) separating off potassium magnesium phosphate, $d_1$) distilling off the pyridine from the aqueous solution which remains, $e_1$) reacting the aqueous solution obtained with calcium chloride and $f_1$) isolating the calcium L-ascorbate-2-monophosphate which crystallizes out.

For more detailed embodiments of this synthesis, reference may be made to the abovementioned patent.

Calcium L-ascorbate-2-monophosphate is readily industrially accessible in the high purity required for use in animal feeds.

To convert the sparingly water-soluble calcium salts into the abovementioned water-soluble salt forms according to the present invention, it is advantageous from a process engineering point of view to bring calcium L-ascorbate-2-phosphate, in particular calcium L-ascorbate-2-monophosphate, into solution in an aqueous medium.

According to EP-A-0 471 805, this can be achieved, for example, by dissolution in aqueous hydrochloric acid. However, a disadvantage of this procedure is that the chloride ions present in this solution mixture adversely affect the purity of the subsequently isolated, water-soluble salts of the ascorbyl 2-phosphoric esters.

It has surprisingly been found that calcium L-ascorbate-2-phosphate dissolves in an aqueous solution of ascorbyl 2-phosphoric esters of the abovementioned formula II, hereinafter referred to as "starting solution", at a pH of from 0.5 to 4, preferably from 1 to 3.5, particularly preferably from 2 to 3. Calcium L-ascorbate-2-monophosphate in particular dissolves under these conditions to form calcium hydrogen L-ascorbate-2-monophosphate.

Such a "starting solution" can be prepared, for example, by deionization of an alkali metal or alkaline earth metal salt solution of ascorbate-2-phosphate, preferably the calcium salt of the formula Ia, particularly preferably by deionizing calcium L-ascorbate-2-monophosphate by means of a strong acid ion exchanger. To achieve the necessary purity of the water-soluble salts of the ascorbyl 2-phosphoric esters of the formula I to be prepared, the "starting solution" used in step a) is advantageously obtained from pure forms of the abovementioned phosphates.

The "starting solution" has a pH of from 0.1 to 4, preferably from 0.5 to 2. The content of ascorbyl 2-phosphoric esters in the "starting solution" is in the range from 5 to 35% by weight, preferably from 10 to 30% by weight, particularly preferably from 15 to 25% by weight.

An advantage of the dissolution process of the present invention [step a) of the preparative method mentioned above] is that no additional extraneous ions are introduced into the solution as contaminants.

In a preferred embodiment, calcium L-ascorbate-2-monophosphate is initially charged as a 5–30% strength by weight, preferably 10–25% strength by weight, particularly preferably 15–22% strength by weight, aqueous suspension and admixed with the "starting solution" containing ascorbyl 2-monophosphoric ester in the abovementioned concentrations until the abovementioned pH is reached to form water-soluble calcium hydrogen L-ascorbate-2-monophosphate.

It is, however, also possible to carry out the dissolution step in the reverse order by adding a 5–30% strength by weight, preferably 10–25% strength by weight, particularly preferably 15–22% strength by weight, aqueous suspension of calcium L-ascorbate-2-monophosphate to the "starting solution".

The dissolved calcium ions present in the solution prepared according to the present invention, containing from 5 to 30% by weight, preferably from 10 to 25% by weight, particularly preferably from 15 to 22% by weight, of calcium hydrogen L-ascorbate-2-monophosphate, which solution may, if desired, be filtered to remove residual undissolved particles, can be removed in a manner known per se. Suitable methods of removing the metal cations are, for example, electrodialysis or preferably deionization over a strong acid ion-exchange resin.

As regards the strong acid ion exchanger used, all commercially available ion-exchange resins of this type can be used without restriction. Examples of strong acid ion exchangers are Lewatit® S100, Amberlite® IR 120, Dowex® HCR and Duolite® C20.

A further advantage of the process of the present invention is the possibility of recycling some of the aqueous solution of ascorbyl 2-phosphoric esters (in the protonated form) obtained after process step b), in particular recycling of part of the eluate obtained after treatment with the strong acid ion exchanger. Such a subs-ream can be used, for example, for dissolving more calcium L-ascorbate-2-monophosphate. The amount of recycled ascorbyl 2-monophosphoric ester solution is dependent on the amount of calcium L-ascorbate-2-monophosphate which is again used. In general, this amount of ascorbyl 2-monophosphoric ester is in the range from 20 to 80% by weight, preferably from 30 to 70% by weight, particularly preferably from 40 to 60% by weight, based on the total amount of the aqueous solution of ascorbyl 2-monophosphoric ester obtained after process step b).

In addition, the aqueous calcium chloride solution obtained in the regeneration of the strong acid ion-exchange resin with aqueous hydrochloric acid solution can be used again for preparing calcium L-ascorbate-2-monophosphate, which additionally represents an ecological and economic advantage of the overall process.

The remainder of the aqueous solution of ascorbyl 2-phosphoric ester obtained after process step b), in the preferred embodiment the remainder of the ion exchange eluate comprising ascorbyl 2-monophosphoric ester, is adjusted to a pH of from 7 to 12, preferably from 8 to 11, particularly preferably from 9.5 to 10.5, by means of sodium, potassium, magnesium or aluminum salts to prepare the water-soluble salts of ascorbyl 2-phosphate. Examples of suitable basic salts are the corresponding hydroxides, oxides or carbonates, preferably hydroxides such as NaOH, KOH, $Mg(OH)_2$ or $Al(OH)_3$, particularly preferably in the form of their concentrated aqueous solutions.

The further treatment of the aqueous solutions of sodium, potassium, magnesium or aluminum L-ascorbate-2-phosphate, in particular of sodium or magnesium L-ascorbate-2-monophosphate, and their isolation is carried out in a manner known per se, for example as described in the Japanese patent applications JP-A-09-077784 and JP-A-02-131494.

In a particular embodiment, addition of a water-miscible organic solvent, for example an alcohol having a chain length of from $C_1$ to $C_5$, a $C_3$–$C_5$-ketone or a cyclic ether, to the abovementioned aqueous solution can be used to change the polarity of the solvent system so that the desired product is precipitated.

The alcohols used for the precipitation are, for example, methanol, ethanol, n-propanol, isopropanol, n-butanol, tert-butanol, preferably methanol or ethanol. Suitable ketones are acetone, methyl ethyl ketone, diethyl ketone, preferably acetone. As cyclic ether, preference is given to using tetrahydrofuran.

The amounts of the abovementioned alcohols, ketones or cyclic ethers used for the precipitation are selected so that the proportion of these organic solvents is from 30 to 90%, preferably from 40 to 80%, particularly preferably from 50 to 75% (v/v), based on the total amount of the mixture.

Depending on the temperature at which the precipitation of the abovementioned salts of ascorbyl 2-phosphate, in particular ascorbyl 2-monophosphate, is carried out, a crystalline or amorphous product is obtained. Details regarding the respective precipitation conditions may be found in the abovementioned Japanese patent applications.

The subsequent isolation and drying of the salts prepared by the process of the present invention are carried out by filtration and drying methods known per se.

The use of pure calcium L-ascorbate-2-phosphate, in particular calcium -ascorbate-2-monophosphate, in the process of the present invention offers the advantageous possibility of passing the solution of sodium, potassium, magnesium or aluminum L-ascorbate-2-phosphate obtained after process step c) directly to a drying process, for example freeze drying or spray drying, preferably spray drying, because of its low proportion of contaminants. This gives a highly pure dry powder of water-soluble vitamin C phosphate.

The salts of ascorbyl 2-phosphate prepared by the process of the present invention, in particular sodium or magnesium L-ascorbate-2-monophosphate, have a purity of from 90 to 99.9%, preferably>95%.

The technical simplicity of the process steps a) to d) of the preparative process of the present invention likewise makes it possible to employ a continuous or semicontinuous plant. Thus, for example, calcium L-ascorbate-2-phosphate can be dissolved by continuous metering into the "starting solution" by means of a metering screw. The subsequent continuous deionization of this solution, preferably over a strong acid ion exchanger, including the regeneration of the ion-exchange resin, is carried out in a manner known per se, for example as described in Ullmanns Encyklopädie der techrischen Chemie, Verlag Chemie (4th Edition, Vol. 13, 1977, pp. 279–346). The neutralization (step c) and the isolation of the desired product (step d) are likewise standard operations known per se which can be carried out continuously in a simple manner.

The following examples illustrate the invention.

EXAMPLE 1

200 g of calcium L-ascorbate-2-monophosphate were suspended in 500 ml of water and admixed with 850 g of a 17% strength by weight solution of ascorbyl 2-monophosphoric ester (protonated form). The pH of the solution was 2.9. The solution was clarified by filtration and the filtrate was passed through a column filled with a strong acid ion exchanger (Lewatit® S100) to remove the calcium ions. After washing with water, the eluates were combined and adjusted to a pH of 9.5 using 50% strength aqueous sodium hydroxide solution. While heating under reflux, a total of 2 1 of methanol were added dropwise to the aqueous solution. The mixture was subsequently cooled to room temperature and the sodium L-ascorbate-2-monophosphate crystals formed were filtered with suction, washed with methanol and dried. This gave 180 g of sodium L-ascorbate-2-monophosphate having a purity of >95%.

EXAMPLE 2

200 g of calcium L-ascorbate-2-monophosphate were, as in Example 1, suspended in 500 ml of water and admixed with 850 g of a 17% strength by weight solution of ascorbyl 2-monophosphoric ester (protonated form). The pH of the solution was 2.9. The solution was clarified by filtration and the filtrate was passed through a column filled with a strong acid ion exchanger (Lewatit® S100) to remove the calcium ions. After washing with water, the total eluate was divided into two equal parts. One half was, as described in Example 1, adjusted to a pH of 9.5 using 50% strength aqueous sodium hydroxide solution. While heating under reflux, a total of 1 1 of methanol was added dropwise to this aqueous solution. The mixture was subsequently cooled to room temperature and the sodium L-ascorbate-2-monophosphate crystals formed were filtered off with suction, washed with methanol and dried. This gave 88 g of sodium L-ascorbate-2-monophosphate having a purity of >95%. The second half of the eluate from the ion-exchange column was used in the next synthesis cycle for again dissolving a suspension of 200 g of calcium L-ascorbate-2-monophosphate in 500 ml of water and processed further as described above.

We claim:

1. A process for preparing salts of ascorbyl 2-phosphoric esters of the formula I,

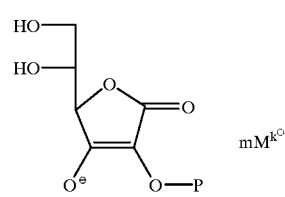

where the variables have the following meanings:

M is sodium, potassium, magnesium, aluminum;

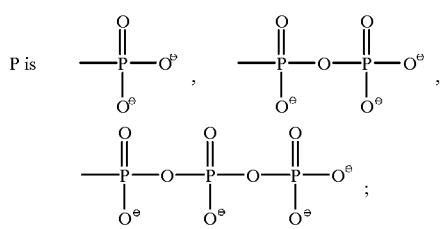

k⊕ is the valence and m are equivalents, where the product of k·m can be from 3 to 5, which comprises
a) dissolving calcium L-ascorbate-2-phosphate of the formula Ia, where P is as defined above, in an aqueous solution of ascorbyl 2-phosphoric esters of the formula II, where $P^1$ is $H_2PO_3$, $H_3P_2O_6$ or $H_4P_3O_9$, at a pH of from 0.5 to 4,

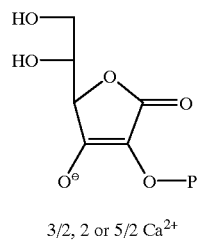

Ia

3/2, 2 or 5/2 $Ca^{2+}$

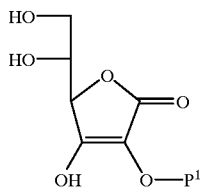

II b) removing the calcium ions from the resulting solution,
c) adjusting the solution which remains to a pH of from 7 to 11 by means of sodium, potassium, magnesium or aluminum salts and
d) isolating the resulting salts of the ascorbyl 2-phosphoric ester of the formula I.

2. A process as claimed in claim 1, wherein, in step b), the calcium ions are removed by adsorption on a strong acid ion-exchange resin.

3. A process as claimed in claim 1, wherein, in step d), a water-miscible, organic solvent is added to the solution obtained after process step c) and the precipitated sodium, potassium, magnesium or aluminum salt of the ascorbyl 2-phosphoric ester of the formula I is isolated.

4. A process as claimed in claim 3, wherein the solvent used in step d) is selected from the group consisting of methanol, ethanol, acetone, methyl ethyl ketone, diethyl ketone and tetrahydrofuran.

5. A process as claimed in claim 1, wherein part of the calcium-free solution obtained after process step b) is again used for dissolving the calcium L-ascorbate-2-phosphate of the formula Ia.

6. A process as claimed in claim 1, wherein the solution obtained after step c) is directly spray dried.

7. A process as claimed in claim 1 which is carried out continuously.

8. A process as claimed in claim 1 used for preparing sodium or magnesium L-ascorbate-2-monophosphate of the formula Ib

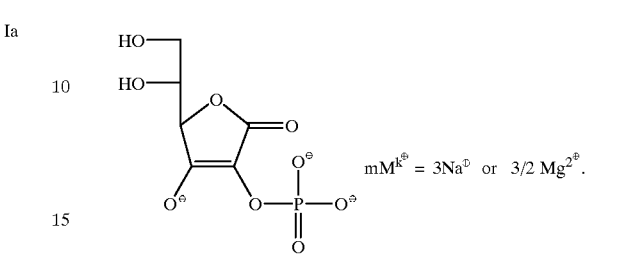

Ib $mM^{k\oplus} = 3Na^{\oplus}$ or $3/2\ Mg^{2\oplus}$.

9. A process as claimed in claim 8, wherein the sodium or magnesium L-ascorbate-2-monophosphates are crystalline or amorphous solids.

10. A process as claimed in claim 8, wherein the starting material used is calcium L-ascorbate-2-monophosphate prepared by
a$_1$) reacting ascorbic acid with phosphorus oxychloride in the presence of pyridine while maintaining a pH of from 12 to 13 by means of an aqueous potassium hydroxide solution,
b$_1$) precipitating the phosphate ions formed in this reaction as potassium magnesium phosphate by means of magnesium chloride in amounts of from about 0.9 to 1.1 mol per mol of phosphate ions,
c$_1$) separating off potassium magnesium phosphate,
d$_1$) distilling off the pyridine from the aqueous solution which remains,
e$_1$) reacting the aqueous solution obtained with calcium chloride and
f$_1$) isolating the calcium L-ascorbate-2-monophosphate which crystallizes out.

11. A process as claimed in claim 2 in which the strong acid ion exchanger is regenerated in an addition step, wherein the aqueous $CaCl_2$ solution produced in the regeneration of the ion-exchange resin with hydrochloric acid can be used again in the process for preparing calcium L-ascorbate-2-monophosphate as defined in claim 10.

* * * * *

UNITED STATES PATENT AND TRADEMARK OFFICE
CERTIFICATE OF CORRECTION

PATENT NO.: 6,121,464

DATED: September 19, 2000

INVENTOR(S): BOETTCHER et al.

It is certified that error appears in the above-identified patent and that said Letters Patent is hereby corrected as shown below:

On the cover page, insert the following assignment information:

--[73] Assignee: BASF Aktiengesellschaft,
            Ludwigshafen, Germany.--

Signed and Sealed this

Twenty-fourth Day of April, 2001

Attest:

NICHOLAS P. GODICI

Attesting Officer        Acting Director of the United States Patent and Trademark Office